(12) United States Patent
Sakhardande et al.

(10) Patent No.: US 8,236,843 B2
(45) Date of Patent: Aug. 7, 2012

(54) ANTI INFLAMMATORY COMPOUNDS

(75) Inventors: Rajiv R. Sakhardande, Mumbai (IN);
Vithal Kulkarni, Pune (IN); Nilesh Wagh, Nasik (IN); Manmohan Nimbalkar, Mumbai (IN); Suhas M. Nadkarni, Mumbai (IN)

(73) Assignee: Elder Pharmaceuticals Ltd. (IN)

( * ) Notice: Subject to any disclaimer, the term of this patent is extended or adjusted under 35 U.S.C. 154(b) by 0 days.

(21) Appl. No.: 13/060,959

(22) PCT Filed: Aug. 24, 2009

(86) PCT No.: PCT/IN2009/000465
§ 371 (c)(1),
(2), (4) Date: May 23, 2011

(87) PCT Pub. No.: WO2010/029576
PCT Pub. Date: Mar. 18, 2010

(65) Prior Publication Data
US 2011/0263543 A1 Oct. 27, 2011

(30) Foreign Application Priority Data
Sep. 2, 2008 (IN) .......................... 1856/MUM/2008

(51) Int. Cl.
*A61K 31/4174* (2006.01)
*C07D 233/64* (2006.01)
*C07D 233/66* (2006.01)

(52) U.S. Cl. .................. 514/398; 548/327.1; 548/335.5; 514/399

(58) Field of Classification Search ................ 548/327.1, 548/335.5; 514/398, 399
See application file for complete search history.

(56) References Cited

U.S. PATENT DOCUMENTS

| | | | |
|---|---|---|---|
| 5,391,732 A | 2/1995 | Bhatnagar et al. | |
| 5,527,919 A | 6/1996 | Bhatnagar et al. | |
| 6,369,236 B1 | 4/2002 | Kleemann et al. | |
| 6,833,381 B2 | 12/2004 | Ikeya et al. | |
| 2004/0097565 A1 | 5/2004 | Terashita et al. | |

FOREIGN PATENT DOCUMENTS

| | | | |
|---|---|---|---|
| EP | 0253310 A2 | | 1/1988 |
| EP | 0253310 A2 | * | 1/1988 |
| EP | 0324377 A2 | | 7/1989 |
| EP | 465368 | | 1/1992 |
| EP | 855392 | | 7/1998 |
| JP | 09165378 | | 6/1997 |
| WO | WO-99/38829 | | 8/1999 |
| WO | WO-01/19788 A2 | | 3/2001 |
| WO | WO-01/82858 A2 | | 11/2001 |
| WO | WO-02/079145 A1 | | 10/2002 |
| WO | WO-2005/051928 A1 | | 6/2005 |
| WO | WO-2005/051929 A1 | | 6/2005 |
| WO | WO-2007/054965 A2 | | 5/2007 |

OTHER PUBLICATIONS

International Application No. PCT/IN2009/000465, International Search Report mailed Oct. 28, 2010, 4 pgs.
Bombardier, C., et al., "Comparison of upper gastrointestinal toxicity of rofecoxib and naproxen in patients with rheumatoid arthritis. VIGOR Study Group.", N Engl J Med., 343(21), (Nov. 23, 2000), 1520-8.
Brune, K., et al., "Minireview: Mechanisms of Action of Anti-Inflammatory Drugs", Gen. Pharmacology, 7, (1976), 27-33.
Penning, T. D, et al., "Synthesis and biological evaluation of the 1,5-diarylpyrazole class of cyclooxygenase-2 inhibitors: identification of 4-[5-(4-methylphenyl)-3-(trifluoromethyl)-1H-pyrazol-1-yl]benze nesulfonamide (SC-58635, celecoxib).", J Med Chem., 40(9), (Apr. 25, 1997), 1347-65.
Prasit, P., et al., "The discovery of rofecoxib, [MK 966, Vioxx, 4-(4'-methylsulfonylphenyl)-3-phenyl-2(5H)-furanone], an orally active cyclooxygenase-2-inhibitor,", Bioorg Med Chem Lett., 9(13), (Jul. 5, 1999), 1773-8.
Riendeau, D., et al., "Etoricoxib (MK-0663); preclinical profile and comparison with other agents that selectively inhibit cyclooxygenase-2.", J Pharmacol Exp Ther., 296(2), (Feb. 2001), 558-66.
Steiner, D. F, et al., "The spontaneous reoxidation of reduced beef and rat proinsulins.", Proc Natl Acad Sci U S A., 60(2), (Jun. 1968), 622-9.
Talley, J. J, et al., "4-[5-Methyl-3-phenylisoxazol-4-yl]—benzenesulfonamide, valdecoxib: a potent and selective inhibitor of COX-2.", J Med Chem., 43(5), (Mar. 9, 2000), 775-7.
Talley, J. J, et al., "N-[[(5-methyl-3-phenylisoxazol-4-yl)-phenyl]sulfonyl]propanamide, sodium salt, parecoxib sodium: A potent and selective inhibitor of COX-2 for parenteral administration.", J Med Chem., 43(9), (May 4, 2000), 1661-3.

* cited by examiner

*Primary Examiner* — Kamal Saeed
*Assistant Examiner* — Janet L Coppins
(74) *Attorney, Agent, or Firm* — Schwegman, Lundberg & Woessner, P.A.

(57) ABSTRACT

Biphenyl compounds of Formula (I) and Formula (II), and their pharmaceutically acceptable salts or solvates or prodrugs, their pharmaceutical compositions, their use and process of preparation are provided. Compounds of Formula (I) and Formula (II) are disclosed to exhibit anti-inflammatory properties.

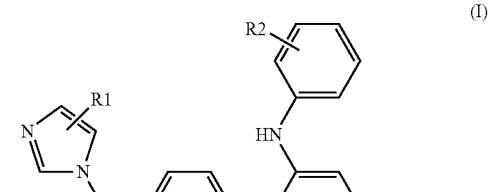

(I)

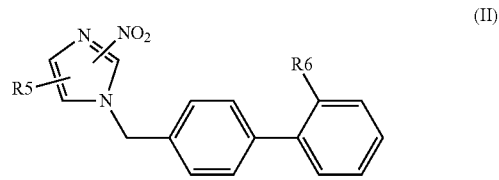

(II)

12 Claims, No Drawings

ANTI INFLAMMATORY COMPOUNDS

PRIORITY CLAIM TO RELATED APPLICATIONS

This application is a U.S. national stage application under 35 U.S.C. §371 of PCT/IN2009/000465, filed Aug. 24, 2009, and published as WO 2010/029576 A2 on Mar. 18, 2010, which claims priority to India Application No. 1856/MUM/08, filed Sep. 2, 2008, which applications and publication are incorporated herein by reference and made a part hereof in their entirety, and the benefit of priority of each of which is claimed herein.

FIELD OF THE INVENTION

The present invention relates to biphenyl imidazole compounds, process for the preparation of biphenyl imidazole compounds, the use of biphenyl imidazole compounds and its pharmaceutically acceptable salts, solvates and prodrugs, to pharmaceutical compositions containing biphenyl imidazole compounds and to the use of biphenyl imidazole compounds and composition in reducing the inflammation in living bodies. The invention also relates to compounds which substantially reduced side effects and method of treating inflammation by administering effective amounts of biphenyl imidazole compounds disclosed by the invention, to the persons in the need.

This invention particularly relates to compounds of the general Formula (I) and Formula (II)

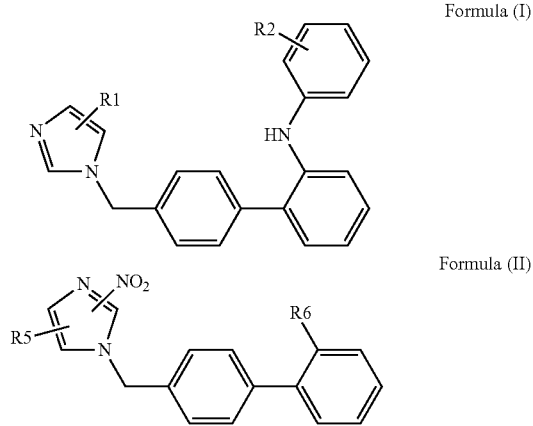

and its pharmaceutically acceptable salts, solvates and prodrugs, to a process of preparation of such compounds, to pharmaceutical compositions containing compounds and their process of preparation and to the use of such compounds and compositions in treating inflammation in living bodies.

BACKGROUND OF THE INVENTION

Inflammation is a complex stereotypical reaction of the body expressing the response to damage of its cells and vascularized tissues. Prostaglandins are primary contributors to conditions of inflammation, pain and fever. Nonsteroidal anti-inflammatory drugs (NSAIDs) act by inhibiting the biosynthesis of prostaglandins. (D. F. Steiner and J. L. Clark, Proc. Natl. Acad. Sci., U.S.A., 60, 622 (1968)). Prostaglandins are biosynthesized with arachidonic acid serving as precursor for an entire cascade of acidic lipids. The biosynthetic reaction for the formation of prostaglandins from arachidonic acids are catalyzed by multienzyme complex commonly referred to as the cyclooxygenase (COX) pathway, COX-1 and COX-2. The reaction proceeds in two stages. In the first stage, the substrate arachidonic acid is transformed into prostaglandins endoperoxide (PGG2 and PGH2) and in the second stage PGG2 and PGH2 are rearranged to form various prostaglandins such as PGD2, PGE2 and PGI2. NSAIDs inhibit the cyclooxygenase step and prevents formation of prostaglandins endoperoxide (PGG2 and PGH2) and thromboxane A2 and other prostaglandins and consequently reduces the signs and symptoms of inflammation (K. Brune, M. Glatt. And P Graf, Gen Pharmacology. 7, 28 (1976). Chronic use of these drugs is associated with side effects such as gastrointestinal irritation (mucosal damage, bleeding) and also at the renal level, thereby limiting their therapeutic potential. Developing safer NSAIDs as selective COX-2 inhibitors is challenge. Several known selective COX-2 inhibitors are Celecoxib (*J. Med. Chem.* 1997, 40(9), 1347-1365), Rofecoxib (*Bioorg. Med. Chem. Lett.* 1999, 9, 1773-1778), Valdecoxib (*J. Med. Chem.* 2000, 43(5), 775-777), Parecoxib Na (*J. Med. Chem.* 2000, 43(9), 1661-1663) and Etoricoxib (*J. Pharmacology. Exp. Ther.* 2002, 296 (2), 558-566).

However, some of selective COX-2 inhibitors exhibit similar side effects such as edema, hypertension as of conventional NSAIDs and the potentially increased risk of thrombosis (*N. Eng. J. Med.* 2000, 343:1520-1528). Gastrointestinal safety of NSAIDs is a major limitation to the use of this class of drugs. There is an increased concern about their cardiovascular adverse effects. The present invention is aimed at inventing novel NSAID compounds useful for the treatment of various types of pain and inflammatory disorder, the process for the preparation of these compounds that have substantially reduced side effects. WO2002079145 and WO01/19788 teaches b enzamide compound in its main claim and its use for the regulation of homeostasis, and for prevention and treatment of thrombus formation and other pathological processes in the vasculature induced by thrombin such as restenosis and inflammation. The compounds have benzamide as essential structural component.

WO9938829 teach novel tricyclic compounds with variable substitution at para position used as an immunosuppressant, an anti allergic agent or a suppressant of the Immunoglobulin E production.

In EP465368 a series of imidazole biphenyl compounds are described as angiotensin II inhibitor and also describes uses in the treatment of arterial hypertension, cardiac insufficiencies, renal insufficiencies and in the prevention of post angioplastic reoccurrences of stenosis, treatment of certain gastro intestinal and gynecological disorders, and in particular for a relaxing effect at the level of the uterus. The essence of the invention is use of imidazole biphenyl as anti-hypertensive.

U.S. Pat. Nos. 5,391,732 and 5,527,919 teach novel process for the preparation of imidazole biphenyl derivatives by disclosing use of Suzuki coupling and use of the compounds in the treatment of ischemic conditions.

JP09165378 teaches $F^{18}$ substituted imidazole biphenyl compounds used as angiotensin II inhibitor.

EP855392 teaches use of imidazole compounds for the treatment or prophylaxis of illnesses caused by ischemic conditions, and also for the production of a medicament for the treatment of impaired respiratory drive. The essence of invention is compound with five membered heterocycles with biphenylsulfonyl substitution with sulfonylcyanamide side chain.

U.S. Pat. No. 6,369,236 teaches use of imidazole biphenyl sulfonyl amide compounds as an intermediate to prepare imidazole biphenyl sulfonyl cynamide compounds.

WO2005051928, WO2005051929, WO2007054965 teach process to prepare tetrazolyl compounds of biphenyl derivatives.

US20040097565 and U.S. Pat. No. 6,833,381 describe the use of heterocyclic compounds having angiotensin II antagonistic activity, e.g. losartan, candesartan as analgesic agent and method of inhibiting tumor necrosis factor-$\alpha$ (TNF-$\alpha$) activity respectively for treating inflammatory diseases.

Surprisingly, it is observed that a series of novel biphenyl imidazole compounds, in particular substituted biphenyl imidazole compounds of Formula (I) and Formula (II) exhibit excellent anti-inflammatory properties and have utility in the treatment and prevention of inflammation in living bodies, animals and human being. It is also noticed that none of the prior art motivates the person skilled in the art to synthesize compounds specifically disclosed by the present invention and make use of the compounds as described in the present invention.

WO2002079145 and WO01/19788 does not teach use of biphenyl imidazole compounds as anti-inflammatory.

WO9938829 does not teach biphenyl compounds disclosed by present invention such as biphenyl imidazole compounds and nitro substituted imidazole compounds.

Although EP465368 teaches a series of imidazole biphenyl compounds, but it does not describe specifically the compounds as disclosed by the present invention which are structurally different and have anti-inflammatory use.

Though U.S. Pat. Nos. 5,391,732 and 5,527,919 teach novel process for the preparation of imidazole biphenyl derivatives, it does not specifically refer to compounds of the present invention as described by present invention.

Although JP09165378 teaches F[18] substituted imidazole biphenyl compounds, it does not teach use of compounds disclosed by present invention for anti-inflammatory applications.

EP855392 neither teach compounds that are taught by present invention nor EP855392 teach use of imidazole compounds for anti-inflammatory applications.

U.S. Pat. No. 6,369,236 although relates to nitro imidazole compounds, it does not teach nitroimidazole substituted compounds as disclosed by present invention nor does it teach use of nitro imidazole compounds for anti-inflammatory applications.

Although WO2005051928, WO2005051929, WO2007054965 teach tetrazolyl compounds, and are silent about nitro imidazole compounds as taught by present invention.

US20040097565 does not teach biphenyl compounds which are the object of the present invention.

Prior art neither specifically teaches the classes of compounds as disclosed by the present invention nor does it motivate the person skilled in the art to prepare the compounds as disclosed by present invention and make use of these compounds for anti-inflammatory applications. Prior art is devoid of teachings related to formulating compositions from the compounds of Formula I and Formula II as disclosed by present invention. Prior art is silent about making use of the compositions containing compounds of Formula I and Formula II for anti-inflammatory applications.

OBJECTIVE OF THE INVENTION

The main object of the present invention is to provide biphenyl imidazole compounds of Formula (I) and Formula (II).

Another object of the invention is to provide process for the preparation of biphenyl imidazole compounds of Formula (I) and Formula (II).

Yet another object of the invention is to provide compositions comprising biphenyl imidazole compounds of Formula (I) and Formula (II).

Yet another object of the invention is to provide process for the preparation of compositions comprising biphenyl imidazole compounds of Formula (I) and Formula (II).

Yet another object of the invention is to provide biphenyl imidazole compounds of Formula (I) and Formula (II) and the compositions comprising biphenyl imidazole compounds of Formula (I) and Formula (II) to treat inflammatory disorders.

Yet another object of the invention is to provide biphenyl imidazole compounds of Formula (I) and Formula (II), process for the preparation of biphenyl imidazole compounds of Formula (I) and Formula (II), compositions comprising biphenyl imidazole compounds of Formula (I) and Formula (II), process for the preparation of compositions comprising biphenyl imidazole compounds of Formula (I) and Formula (II) and the use of compounds of Formula (I) and Formula (II) and the compositions thereof to treat any inflammation in living bodies.

Yet another object of the invention is to provide biphenyl imidazole compounds of Formula (I) and Formula (II) that have anti-inflammatory effect yet have substantially reduced side effects such as gastrointestinal irritation, ulcerogenicity exhibited by known NSAIDs.

Yet another object of the invention is to provide a method of treating inflammation mediated diseases, by administering an effective amount of a compound of Formula (I) or Formula (II), or salt or solvates or prodrugs thereof, to a living bodies in need of such treatment.

SUMMARY OF THE INVENTION

Present invention discloses
i) Compounds of Formula (I):

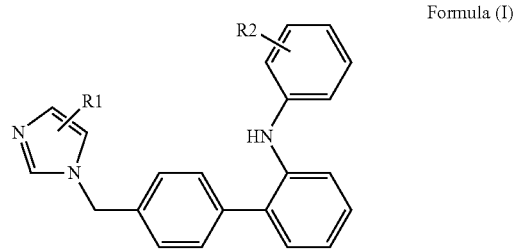

Formula (I)

Wherein,
R1 is one or more of H, —NO$_2$, R4, —O—(CH$_2$) n-R4 wherein n=0 to 5, —NH$_2$, —SO$_2$NH$_2$, —NHSO$_2$—R4, halo, —COOH, acyl, —CN, optionally substituted amine, —SO$_2$NHR4;
R2 is H, —O—(CH$_2$)n-R4 wherein n=0 to 5, —NO$_2$, —SO$_2$NH$_2$, —NHSO$_2$—R4, —CN, —COOH, halo, optionally substituted amine, R4, cycloalkyl group, alkyl thio, acyl, substituted or unsubstituted heterocyclic group, alkoxy carbonyl, aryloxy, aryloxy carbonyl, substituted or unsubstituted amide;

R4 is any substituted or unsubstituted alkyl;

and their pharmaceutically acceptable salts, solvates or prodrugs to treat inflammation; and compounds of Formula (II)

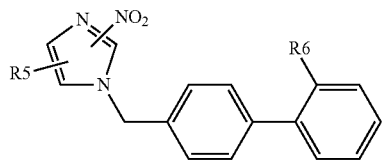

Formula (II)

wherein,

R5 is one or more of H, halo, $NO_2$, R4, alkoxy carbonyl, —O—$(CH_2)$n-R4 wherein n is 0 to 5, —COOH, —$SO_2NH_2$, —$NHSO_2$—R4, aryl, cycloalkyl, benzyl or substituted benzyl optionally substituted on phenyl ring with at least one halogen, CN, —$(CH_2)$m-R7 wherein m is 0 to 5, —$(CH_2)$p-OC(O)R4 wherein p is 1 to 5, optionally substituted amine;

R6 is one or more of CN, H, halo, $NO_2$, R4, —$NH_2$, alkoxy carbonyl, —O—$(CH_2)$n-R4 wherein n is 0 to 5, —COOH, —$SO_2NH_2$, —$NHSO_2$—R4, $SO_2$—NH—R4, aryl, substituted or unsubstituted heterocyclic group, —$CH_2COOH$, —$CH_2COOR4$, —$SO_3H$, —$PO_3H$, substituted or unsubstituted amide, —$CH_2$—R7, —CONH—R7 wherein R7 is any substituted or unsubstituted heterocyclic group;

R4 is any substituted or unsubstituted alkyl.

and ii) process for the preparation of compounds (I) and compound (II); and iii) compositions comprising compound (I) and compound (II); and iv) process for the preparation of compositions comprising compound (I) and compound (II); and v) use of compound (I) and compound (II), compositions of compound (I) and compound (II) for anti-inflammatory applications.

Compounds of this invention are superior to compounds of known NSAID such as diclofenac, celecoxib and tolfenamic acid.

DETAILED DESCRIPTION OF THE INVENTION

According to the invention there are provided compounds of Formula (I) and Formula (II), process for the preparation of compounds of Formula (I) and Formula (II), compositions comprising compounds of Formula (I) and Formula (II), process to prepare the compositions comprising compounds of Formula (I) and Formula (II), use of the compounds of Formula (I) and Formula (II), compositions comprising compounds of Formula (I) and Formula (II) for the treatment of inflammation in the living bodies.

It was surprisingly found that compounds of above Formula (I) and Formula (II) have a good anti inflammatory activity and exhibit substantially reduced side effects such as gastrointestinal irritation, ulcerogenicity exhibited by known NSAIDs.

The definition of each symbol of the compounds described in the present specification is explained in the following:

In the aforementioned formulae,

The term H is hydrogen atom. $NO_2$ is nitro group. $NH_2$ is amino group. $SO_2NH_2$ represents sulfonamide. $SO_2$—NH—R4 is substituted sulfonamide in which R4 is as described herein.

CN is cyano. Halo or halogen represents Cl, Br, F, I. COOH means carboxy group. Unsubstituted alkyl means straight and branched chain saturated hydrocarbon radicals having $C_{1-6}$ carbon atoms such as methyl, ethyl, propyl, n-butyl, 1-methylethyl, 2-methylpropyl, 1,1-dimethylethyl, n-pentyl, dimethylpropyl, n-hexyl, 2-methylpentyl, 3-methylpentyl etc.

Substituted alkyl means alkyl group substituted with one or more of same or different substituents such as halo, carboxy, cycloalkyl, aryl, nitro, cycloalkenyl, alkoxy, alkoxycarbonyl, aralkoxycarbonyl, alkyl, aralkyl, exemplary groups includes methyl, trifluoromethyl, acyl, carboxymethyl, methoxy carbonyl ethyl, benzyloxy carbonyl methyl. O—$(CH_2)$n-R4 where in n=0 to 5 is alkoxy in which R4 is as described herein includes methoxy, ethoxy, propoxy, butoxy etc.

—$NHSO_2$—R4 is alkyl sulfonyl amino such as methyl sulfonyl amino, ethyl sulfonyl amino, iso-propyl sulfonyl amino, n-propyl sulfonyl amino.

Acyl means —C(O)H or alkyl-CO, exemplary groups includes formyl, acetyl, propanoyl, and butanoyl.

Optionally substituted amine is either amine or alkyl amine or aryl amine such as methyl amine, ethyl amine, dimethyl amine, diethyl amine, phenyl amine, naphthyl amine, benzyl amine, diphenyl amine.

Cycloalkyl means a non aromatic ring system of about C3 to C10 carbon atoms, preferably of C5 to C10 carbon atoms, exemplary groups include cyclopentyl, cyclohexyl, and cycloheptyl. Alkylthio means an alkyl-S group wherein alkyl group is as defined herein, exemplary alkylthio groups include methylthio, ethylthio, and iso-propylthio.

Substituted or unsubstituted heterocyclic group includes 5 to 7 membered saturated cyclic ring containing one or more hetero atoms selected from nitrogen atom, sulfur atom and oxygen atom, exemplary includes piperidino, morpholino, pyrrolidino. Also it includes 5 to 10 membered aromatic ring containing, besides carbon atom, one or more hetero atoms selected from nitrogen atom, sulfur atom and oxygen atom, exemplary includes thienyl, pyridyl, indolyl, quinolyl, isoquinolyl, imidazole, tetrazole.

Substituted heterocyclic means heterocyclic group substituted with one or more of same or different substituents such as halo, carboxy, cycloalkyl, aryl, nitro, cycloalkenyl, alkoxy, alkoxycarbonyl, aralkoxycarbonyl, alkyl, aralkyl, exemplary groups include methyl, trifluoromethyl, acyl, carboxymethyl, methoxy carbonyl ethyl, benzyloxy carbonyl methyl. Alkoxy carbonyl means —COOR4 wherein R4 is as defined herein, exemplary includes methoxy carbonyl, ethoxy carbonyl, and propoxy carbonyl.

Aryloxy means an aryl-O— group wherein the aryl group is phenyl, naphthyl, exemplary includes phenoxy, 2-naphthyloxy.

Aryloxy carbonyl means an aryl-O—C(O)— group, exemplary aryloxy carbonyl groups include phenoxy carbonyl and naphthyloxy carbonyl.

Substituted or unsubstituted amide is —CONH—R4 wherein R4 is as defined herein and —CONH—R7 wherein R7 is as defined herein, —$(CH_2)$p-OC(O)R4 wherein p is 1 to 5 in which R4 is as defined herein.

—$SO_3H$ is sulfonic acid. —$PO_3H$ is phosphoric acid. —$CH_2COOR4$ in which R4 is as defined herein.

The term pharmaceutically acceptable salt as used herein refers to salts of compounds of Formula (I) and Formula (II). Typical pharmaceutically acceptable salts include those salts prepared by reaction of compounds of present invention with a pharmaceutically acceptable organic or inorganic acids or bases. Such salts are known as acid and base addition salt.

Acids commonly employed to form acid addition salts are inorganic acids such as hydrochloric acid, hydrobromic acid, sulfuric acid, phosphoric acid and the like, and organic acids such as p-toluenesulfonic, methanesulfonic, oxalic acid, carbonic acid, succinic acid, citric acid, benzoic acid, acetic acid, and the like. Examples of such pharmaceutically acceptable salts are sulfate, pyrosulfate, bisulfate, sulfite, bisulfite, phosphate, monohydrogen phosphate, dihydrogen phosphate, pyrophosphate, bromide, acetate, propionate, acrylate, formate, oxalate, malonate, succinate, tartarate, methane sulfonate, propane sulfonate, naphthalene-1-sulfonate, naphthalene-2-sulfonate, mandelate, mesylate, and the like.

Base addition salts include those derived from inorganic bases, such as ammonium or alkali or alkaline earth metal hydroxides, carbonates, bicarbonates, and the like. Examples of such pharmaceutically acceptable salts are sodium hydroxide, potassium hydroxide, ammonium hydroxide, potassium carbonate, sodium carbonate, calcium hydroxide, calcium carbonate, and the like. The term solvates includes existence of compounds in combination with solvent such as water, ethanol and isopropanol. The invention further encompasses methods employing pharmaceutically acceptable solvates of the compounds of Formula (I) and Formula (II).

According to another aspect of the present invention there is provided a method of treating inflammation mediated diseases, by administering an effective amount of a compound of Formula (I) or Formula (II), or salt or solvates or prodrugs thereof, to a living bodies in need of such treatment.

Thus, according to another aspect of the invention there is provided the use of a compound of Formula (I) or Formula (II) or salt or solvates or prodrugs in the preparation of composition for use in the treatment of inflammation with reduced side effects such as gastrointestinal irritation, ulcerogenicity. The compound is suitably formulated as a pharmaceutical composition for use in this way.

The solid dosage forms such as tablets are prepared by dry or weight granulating the compound of the Formula (I) or Formula (II) with suitable excipients such as diluents, glidents, lubricants, stabilizers followed by compression and optional coating. The tablets of compounds of the Formula (I) or Formula (II) can be provided in immediate release or extended release form.

Compounds of the Formula (I) or Formula (II) can be formulated in capsule dosage form by filling the compounds of the Formula (I) or Formula (II) in capsules either with suitable excipients or without excipients.

Compounds of the Formula (I) or Formula (II) can be formulated in liquid compositions by suspending, dissolving, emulsifying, solvating in suitable solvent such as water, glycerin, physiologically acceptable alcohols. Depending upon the ingredients the liquid can be used for either internal consumption or external application.

Compounds of the Formula (I) or Formula (II) can be formulated in semi-solid compositions either for external application or in the form of suppositories or pessaries. External applications can be formulated by incorporating compounds of the Formula (I) or Formula (II) into aqueous, non-aqueous bases or oily bases. Known non-greasy bases can also be used for incorporating compounds of the Formula (I) or Formula (II), to prepare compositions commonly known as creams, lotions, snow, lip-sticks.

The compositions of the invention may be in a form suitable for oral use, for topical use, for administration by inhalation, for administration by insufflation or for parenteral administration.

The composition of the invention may be obtained by conventional procedures using conventional pharmaceutical excipients, well known in the art.

The amount of active ingredient that is combined with one or more excipients to produce a single dosage form will necessarily vary depending upon the host treated and the particular route of administration to humans will generally contain, for example, from 0.001 mg to 5 gm of active agent compounded with an appropriate and convenient amount of excipients which may vary from about 5 to 98 percent by weight of the total composition.

A compound of the invention, or a salt thereof, may be prepared by the process illustrated hereto in the application. Such processes are illustrated in the following representatives schemes in which variable groups have any of the meanings defined herein unless stated otherwise. Functional groups may be protected and deprotected using conventional methods. Protection and deprotection of functional groups may be referred from T. W. Greene and P. G. M. Wuts, "Protective Groups in Organic Synthesis", Fourth Edition, John Wiley & Sons, New York, 2007.

The following examples are for illustration purposes and are not intended to limit the scope of this application. In the following non-limiting examples, unless otherwise stated:

Evaporation was carried out by rotary evaporation in vacuum and workup procedures were carried out after removal of residual solids such as drying agents by filtration.

The structures of the end products of intermediates and compounds of Formula (I) and Formula (II) were confirmed by nuclear magnetic resonance (NMR) and mass spectral techniques and infra red (IR). Intermediates were conventionally characterizes and purity was assessed by thin layer chromatography (TLC), high performance chromatography (HPLC), infrared (IR) or NMR.

Scheme I

Preparation for compounds of Formula (I)

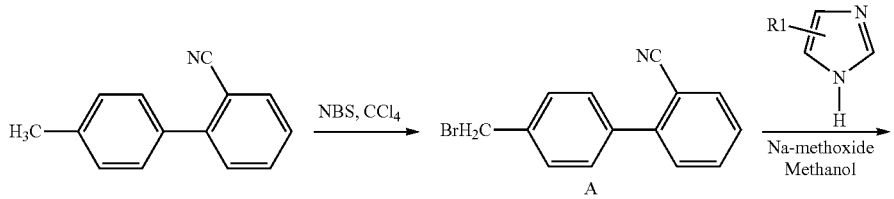

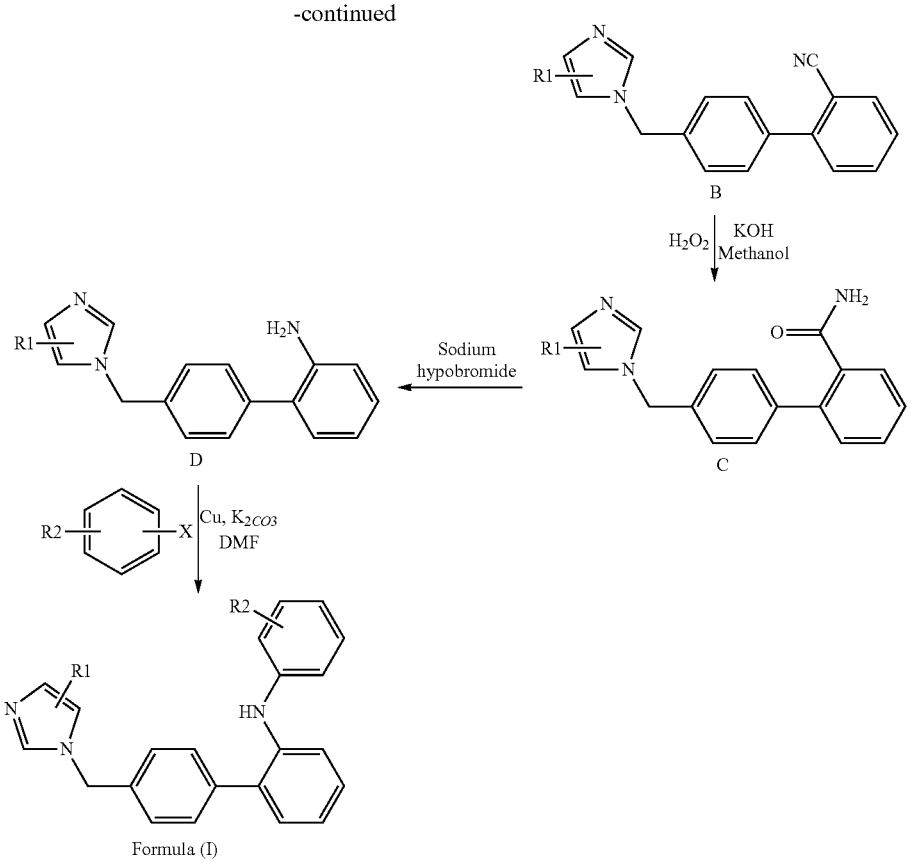

Formula (I)

General Procedure for the Preparation of Compounds A

In a 250 ml assembly equipped with reflux condenser, stirrer and calcium chloride guard tube, charge equimolar amount of 4'-methyl-2-cynobiphenyl and N-bromosuccinamide in carbon tetrachloride. To the reaction mixture 0.3 mole equivalent of benzoyl peroxide was added. The reaction mixture was refluxed for 12 hours and the progress of the reaction was monitored on TLC. After the completion of reaction, the reaction mixture was filtered. The filtrate was distilled under vacuum. Semisolid residue was collected and recrystalised from acetone:hexane mixture.

General Procedure for the Preparation of Compounds B

Charge equimolar amount of 4-bromomethyl-biphenyl-2-carbonitrile (A) and sodium methoxide followed by addition of equimolar amount of substituted imidazole in methanol and refluxed. After the completion of reaction, the reaction mixture was filtered and the mother liquor was charged to cold water. The solid residue was filtered, washed with cold water and recrystalised from ethanol. The obtained compound is compound B.

General Procedure for the Preparation of Compounds C

Charge 0.025 moles of compound B in methanol (25 ml), followed by 0.675 moles of hydrogen peroxide and stirred. To the reaction mixture 0.05 moles of potassium hydroxide was added. Control the exothermicity. The reaction mixture was slowly refluxed. After completion of reaction, the reaction mixture was used in situ. The reaction mixture was treated with water and extracted with ethyl acetate. The organic layer was washed with saturated brine solution, dried over sodium sulfate, filtered and evaporated to dryness. The crude product was used in next step.

General Procedure for the Preparation of Compounds D

Charge 0.012 moles of compound C and 0.3 moles sodium hypobromide solution and stirred at 0-5° C. To the reaction mixture 2.9 gm of sodium hydroxide was added and heated to 70° C. The progress of reaction was monitored by TLC. After the completion of the reaction, reaction mixture was filtered. The solid was recrystalised from methylene dichloride.

General Procedure for the Preparation of Compounds of Formula (I)

Charge 0.0065 moles of compound D in 25 ml dimethylformamide. To the reaction mixture 0.00195 moles of copper was added, followed by 0.0065 moles of potassium carbonate. To this mixture, 0.0065 moles of substituted or unsubstituted phenyl halo compound was added and refluxed. After the completion of reaction, reaction mixture was filtered. The filtrate was added to cold water. The solid residue was filtered and recrystalised from methanol.

Scheme Ia

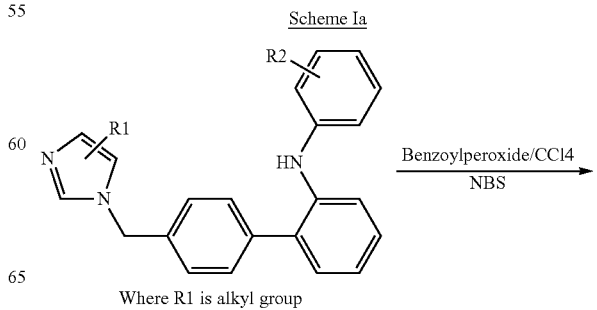

Where R1 is alkyl group

-continued

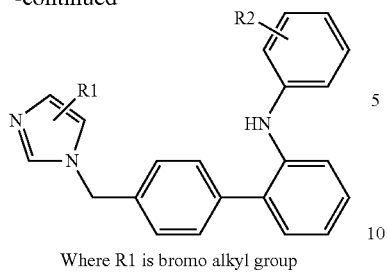

Where R1 is bromo alkyl group

Charge equimolar amount of compound of Formula (I) (wherein R1 is alkyl group) and N-bromosuccinamide in carbon tetrachloride, followed by 0.3 mole equivalent of benzoyl peroxide. The reaction mixture was refluxed. The progress of the reaction was monitored on TLC. After completion of reaction, the reaction mixture was filtered. The filtrate was concentrated under vacuum. The semisolid residue was collected and the product is compound of Formula (I) (wherein R1 is bromo alkyl group).

Scheme IB

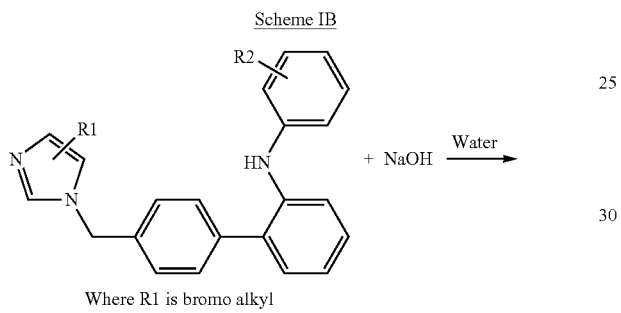

Where R1 is bromo alkyl

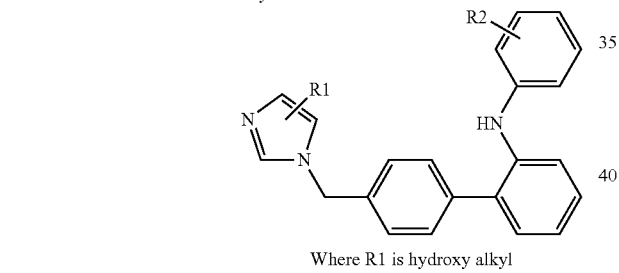

Where R1 is hydroxy alkyl

Charge 0.0073 mole of compound of Formula (I) (wherein R1 is bromo alkyl) in a solution containing 0.11 mole of sodium hydroxide in 25 ml of water. The reaction mixture was stirred for 15 minutes and heated to 50° C. The progress of the reaction was monitored on TLC. After completion of reaction, the reaction mixture was filtered. The solid residue was collected and recrystalised from acetone. The solid obtained is compound of Formula (I) (wherein R1 is hydroxyalkyl group).

EXAMPLES

Example 1

(a) 4'-Bromomethyl-biphenyl-2-carbonitrile (A)

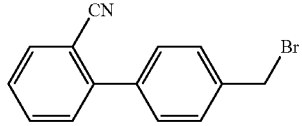

M.P.: 116-118° C.
IR (KBr) cm$^{-1}$: 3000, 2880, 2260, 550.
$^1$H NMR δppm in CDCl$_3$: 7.12~7.62 (8H), 4.52 (2H).

(b) 4'-(2-Methyl-imidazol-1-ylmethyl)-biphenyl-2-carbonitrile (B)

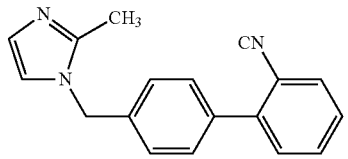

M.P.: 164-166° C.
IR (KBr pellet) cm$^{-1}$: 3153, 2874, 2274.

(c) 4'-(2-Methyl imidazol-1-ylmethyl)-biphenyl-2-carboxylic acid amide (C)

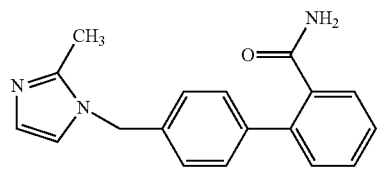

M.P.: 181-182° C.
IR (KBr pellet) cm$^{-1}$: 3365, 3059, 1680, 1410.

(d) 4'-(2-Methyl imidazol-1-ylmethyl)-biphenyl-2-ylamine (D)

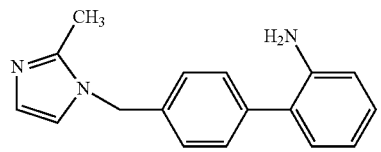

M.P.: 123-126° C.
IR (KBr pellet) cm$^{-1}$: 3410, 3059, 1430.

(e) (4-Methoxy phenyl)-[4'-(2-methyl imidazol-1-ylmethyl)-biphenyl-2-yl]amine

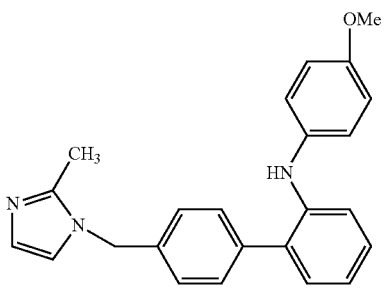

In a 100 ml assembly equipped with reflux condenser, stirrer and calcium chloride guard tube charge 0.0065 moles of 4'-(2-methyl imidazol-1-ylmethyl)-biphenyl-2-ylamine in 25 ml dimethylformamide. To the reaction mixture 0.00195 moles of copper was added, followed by 0.0065 moles of potassium carbonate. To this mixture, 0.0065 moles of 4-methoxy bromobenzene was added and heated to 140° C. for 8-10 hours. After the completion of reaction, reaction mixture was filtered. The filtrate was added to cold water. The solid residue was filtered and recrystalised from methanol.
M.P.: 127-132° C.
IR (KBr pellet) cm$^{-1}$: 3343, 3086, 2993.

(f) [4'-(2-Bromomethyl imidazol-1-ylmethyl)-biphenyl-2-yl]-(4-methoxyphenyl)-amine

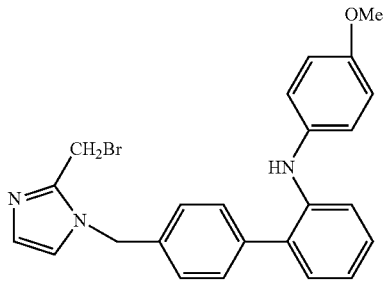

Nature: Oily Compound
IR (KBr pellet) cm$^{-1}$: 3357, 2993, 2930, 712.

(g) {1-[2'-(4-Methoxyphenylamino)-biphenyl-4-ylmethyl]-1H-imidazol-2-yl}-methanol

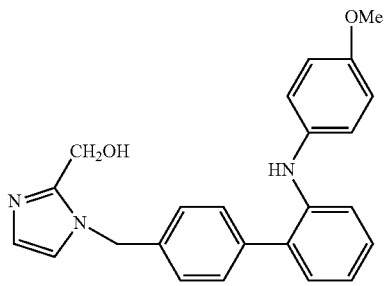

M.P.: 89-92° C.
IR (KBr pellet) cm$^{-1}$: 3410, 3383, 2979.
$^1$H NMR (CDCl$_3$) (δ ppm): 6.650-7.862 (12H), 8.358 (1H), 8.381 (1H), 4.759 (2H), 4.218 (2H), 3.487 (3H), 3.831 (1H), 2.319 (1H).

Example 2

(a) 4'-(2-Methyl-4-nitro-imidazol-1-ylmethyl)-biphenyl-2-carbonitrile (B)

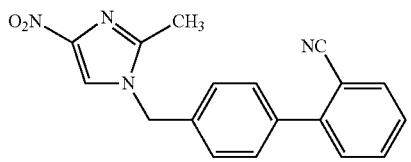

M.P.: 113-116° C.
IR (KBr pellet) cm$^{-1}$: 3020, 2220, 1410.

(b) 4'-(2-Methyl, 4-nitro imidazol-1-ylmethyl)-biphenyl-2-carbxamide (C)

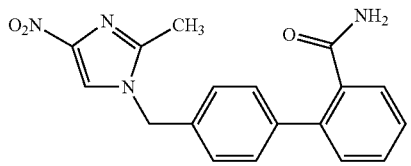

Nature: Oily Compound (c) 4'-(2-methyl, 4-nitro imidazol-1-ylmethyl)-biphenyl-2-ylamine (D)

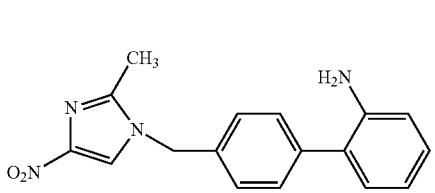

M.P.: 201-203° C.

(d) 4-[4'-(2-Methyl-4-nitro-imidazol-1-ylmethyl)-biphenyl-2-ylamino]-benzene sulfonamide

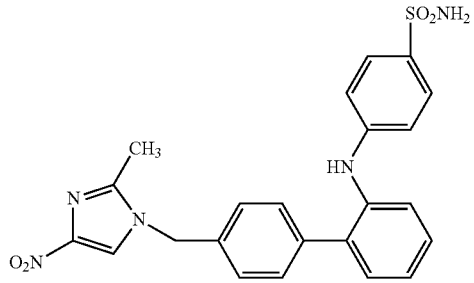

M.P.: 171-173° C.
IR (KBr pellet) cm$^{-1}$: 3443, 3314, 3020, 1456.
$^1$H NMR (DMSO-d$_6$) (δ ppm): 7.112-7.877 (12H), 8.063 (1H), 4.679 (2H), 3.857 (2H), 3.319 (1H), 2.334 (3H).

(e) [4'-(2-Bromomethyl-4-nitroimidazo-1-ylmethyl)-biphenyl-2-yl](4-sulfonamidophenyl)-amine

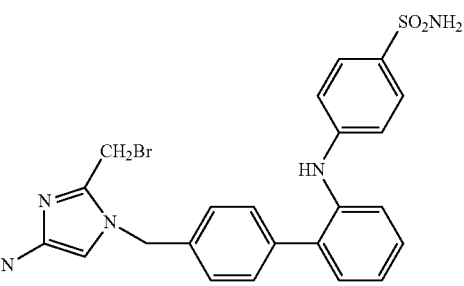

Nature: Oily Compound
IR (KBr pellet) cm$^{-1}$: 3323, 3250, 1468, 690.

(g) 4-[4'-(2-Hydroxymethyl-4-nitro-imidazol-1-ylmethyl)-biphenyl-2-ylamino]-benzenesulfonamide

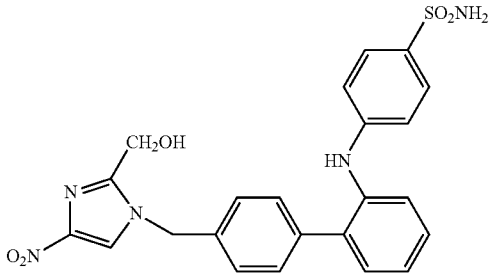

M.P.: 154-155° C.
IR (KBr pellet) cm$^{-1}$: 3453, 3389, 3246, 3022, 1468.
$^1$H NMR (DMSO-d$_6$) (δ ppm): 6.524-7.502 (12H), 7.850 (1H), 4.784 (2H), 4.234 (2H), 3.782 (2H), 3.174 (1H), 2.392 (1H).

TABLE 1

| | Compounds of Formula (I) | | | |
|---|---|---|---|---|
| | | Substitute | | |
| Sr. No. | Structure | R1 | R2 | Characteristics |
| 1 | (4-Methoxy phenyl)-[4'-(2-methyl imidazol-1-ylmethyl)-biphenyl-2-yl]-amine | CH3 | OMe | M.P: 127-132° C. IR (KBr pellet) cm$^{-1}$: 3343, 3086, 2993. |
| 2 | [4'-(4-Nitro-2-methyl imidazole-1-ylmethyl)-biphenyl)-2-yl]-amine | CH3 | H | M.P: 101-103° C. IR (KBr pellet) cm$^{-1}$: 3325, 3032, 2956. $^1$H NMR δ ppm in CDCl$_3$: 7.174-7.92 (13H), 8.103 (1H), 8.074 (1H), 4.927 (2H), 3.487 (1H), 2.396 (3H). |
| 3 | [4'-(4-Nitro-2-methyl imidazol-1-ylmethyl)-biphenyl-2-yl]-phenyl-amine | NO$_2$, CH$_3$ | H | M.P: 134-136° C. IR (KBr pellet) cm$^{-1}$: 3314, 3020, 1456. $^1$H NMR δ ppm in CDCl$_3$: 6.815-7.476 (13H), 7.796 (1H), 4.64 (2H), 3.226 (1H), 2.32 (3H). |
| 4 | 4-[4'-(4-Nitro-2-methyl imidazol-1-ylmethyl)-biphenyl-2-ylamino]-benzene sulfonamide | NO$_2$ | SO$_2$—NH$_2$ | M.P: 171-173° C. IR (KBr pellet) cm$^{-1}$: 3443, 3314, 3020, 1456. $^1$H NMR (DMSO-d$_6$) (δ ppm): 7.112-7.877 (12H), 8.063 (1H), 4.679 (2H), 3.857 (2H), 3.319 (1H), 2.334 (3H). |
| 5 | [4'-(2-Bromomethyl imidazol-1-ylmethyl)-biphenyl-2-yl]-(4-methoxyphenyl)-amine | CH$_2$—Br | OMe | Nature: Oily compound IR (KBr pellet) cm$^{-1}$: 3357, 2993, 2930, 712. |
| 6 | [4'-(2-Bromomethyl-4-nitroimidazo-1-ylmethyl)-biphenyl-2-yl](4-sulfonamidophenyl)-amine | NO$_2$, CH$_2$—Br | SO$_2$—NH$_2$ | Nature: Oily compound IR (KBr pellet) cm$^{-1}$: 3323, 3250, 1468, 690. |
| 7 | 4-[4'-(2-Hydroxymethyl-4-nitro-imidazol-1-ylmethyl)-biphenyl-2-ylamino]-benzenesulfonamide | NO$_2$, CH$_2$—OH | SO$_2$—NH$_2$ | M.P: 154-155° C. IR (KBr pellet) cm$^{-1}$: 3453, 3389, 3246, 3022, 1468. $^1$H NMR (DMSO-d$_6$) (δ ppm): 6.524-7.502 (12H), 7.850 (1H), 4.784 (2H), 4.234 (2H), 3.782 (2H), 3.174 (1H), 2.392 (1H). |
| 8 | {1-[2'-(4-Methoxyphenylamino)-biphenyl-4-ylmethyl]-1H-imidazol-2-yl}-methanol | CH$_2$—OH | OMe | M.P: 89-92° C. IR (KBr pellet) cm$^{-1}$: 3410, 3383, 2979. $^1$H NMR δ ppm in CDCl$_3$: 6.650-7.862 (12H), 8.358 (1H), 8.381 (1H), 4.759 (2H), 4.218 (2H), 3.487 (3H), 3.831 (1H), 2.319 (1H), |

General Procedure for Compounds of Formula (II)

Scheme II

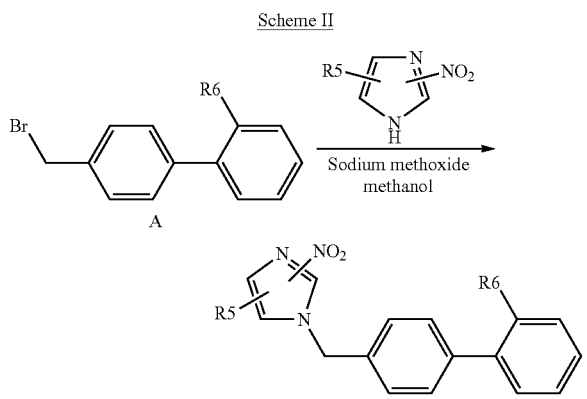

In a 250 ml assembly equipped with reflux condenser, stirrer, and calcium chloride guard tube, charge equimolar amount of suitably substituted 4-bromo methyl biphenyl compound (A) and sodium methoxide was added, followed by addition of equimolar amount of corresponding substituted imidazoles in methanol. The reaction mixture was refluxed. After completion of the reaction, it was filtered. The filtrate was added to cold water. The solid residue was filtered and washed with cold water and recrystalised from ethanol.

Scheme III

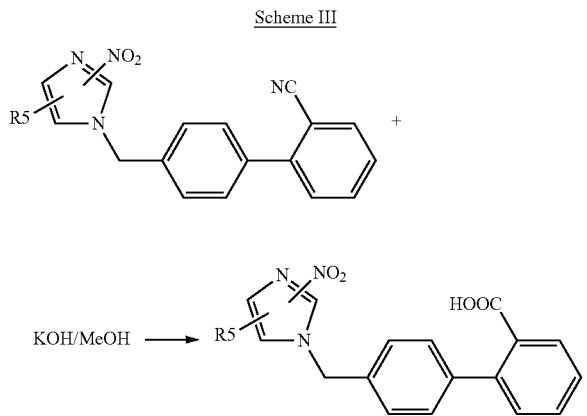

Charge one molar concentration of compounds of Formula (II) where in R6 is COOH in 50 ml methanol. To the reaction mixture fourteen molar concentration of potassium hydroxide was added. The reaction mixture was refluxed. After the completion of reaction, reaction mixture was filtered. The filtrate was then added to cold water. The solid residue was filtered, washed with cold water and recrystalised from ethanol.

Scheme IV

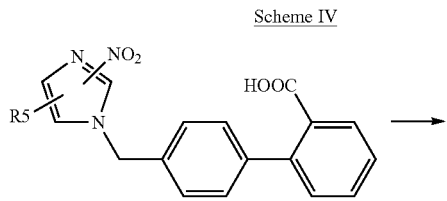

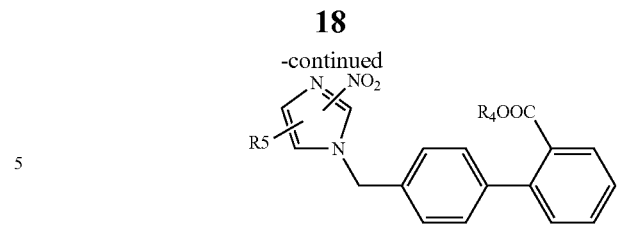

Charge 1 mole of compounds of Formula II where in R6 COOH in methylene chloride and catalytic amount of DMF. The reaction mixture was cooled to 15° C. and slowly added (3 mole equivalent) thionyl chloride. The reaction mixture was heated to reflux and checked for the completion of the reaction. The reaction mixture was cooled to 10° C. and slowly added required alcohol. The reaction mixture was further stirred at room temperature for 1 hour. The reaction mixture was treated with methylene dichloride and washed with water, 5% sodium bicarbonate solution and again with water. The organic layer was dried over sodium sulfate, filtered and evaporated to dryness. The crude product was crystallized from methanol.

Scheme V

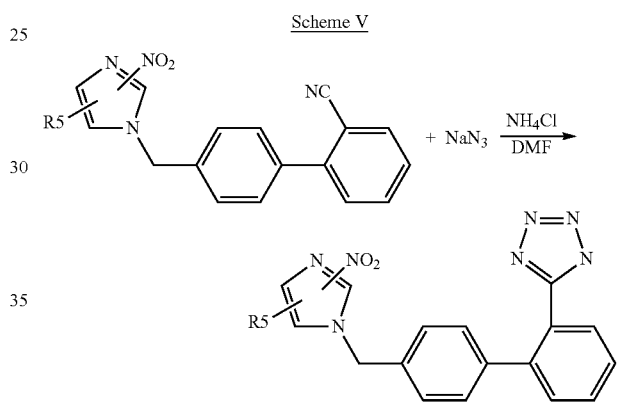

Charge equimolar concentration of compounds of Formula (II) (where in R6 is CN), and sodium azide and catalytic amount of ammonium chloride in DMF. The reaction mixture was refluxed. After the completion of the reaction, the reaction mixture was filtered. The filtrate was added to cold water. The solid residue was filtered and washed with cold water, and purified by column chromatography.

Examples

Example 3

(a) 4'-Bromomethyl-biphenyl-2-carbonitrile (A)

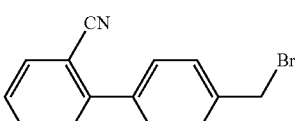

M.P.: 116-118° C.
IR (KBr) cm$^{-1}$: 3000, 2880, 2260, 550.
$^1$H NMR δppm in CDCl$_3$: 7.12~7.62 (8H), 4.52 (2H).

(b) 4'-(5-Bromo-2-methyl-4-nitro-imidazol-1-ylm-ethyl)-biphenyl-2-carbonitrile

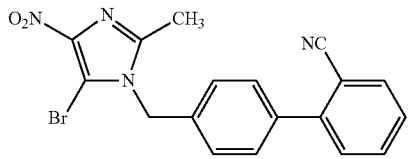

M.P.: 158-162° C.
IR (KBr pellet) cm$^{-1}$: 3050, 2250, 1550, 1340, 775.
$^1$H NMR (CDCl$_3$) (δ ppm): 7.970-7.277 (8H), 5.473 (2H), 2.428 (3H).

(c) 4'-(5-Bromo-2-methyl-4-nitro-imidazol-1-ylm-ethyl)-biphenyl-2-carboxylic acid

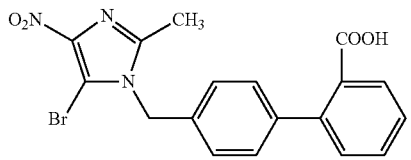

M.P.: 222-225° C.
IR (KBr pellet) cm$^1$: 3100, 3025, 1720, 1535, 1350, 831
$^1$H NMR: (CDCl$_3$) (δ ppm): 12.806 (1H), 7.738-7.197 (8H), 5.400 (2H), 2.396 (3H).

Example 4

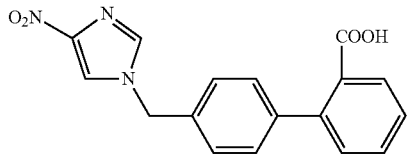

In a 250 ml assembly equipped with reflux condenser, stirrer and calcium chloride guard tube, 0.01 mole of 4'-(4-nitro-imidazol-1-ylmethyl)-biphenyl-2-carbonitrile is charged in 100 ml methanol. To the reaction mixture 0.14 mole of potassium hydroxide was added. The reaction mixture was heated to a temperature of 60° C.-65° C. for 10 to 12 hours. After the completion of reaction, reaction mixture was filtered. The filtrate was then added to cold water. The solid residue was filtered, washed with cold water and recrystalised from ethanol.

M.P: 202-204° C.
IR (KBr) cm$^{-1}$: 3000, 2960, 2880, 2700, 1710, 1332.
$^1$H NMR δ ppm in CDCl$_3$: 11 (1H), 7.99 (1H), 7.12~7.66 (10H), 4.62 (2H).

Example 5

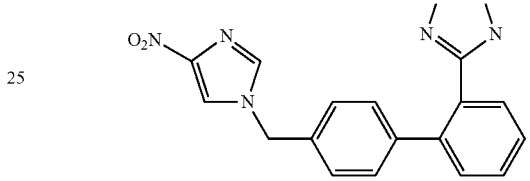

In a 250 ml assembly equipped with reflux condenser, stirrer and calcium chloride guard tube, equimolar concentration of 4'-(4-nitro-imidazol-1-ylmethyl)-biphenyl-2-carbonitrile and sodium azide and catalytic amount of ammonium chloride was charged in dimethylformamide. The reaction mixture was heated to 135-140° C. for 14-16 hours. After the completion of the reaction, the reaction mixture was filtered. The filtrate was added to cold water. The solid residue was filtered and washed with cold water, and purified by column chromatography.

M.P: 189-192° C.
IR (KBr pellet) cm$^{-1}$: 3310, 2960, 1710, 1351.
$^1$H NMR δ ppm in CDCl$_3$: 8.1 (1H), 7.99 (1H), 7.12~7.66 (9H), 5.01 (2H).

TABLE 2

| | Compounds of Formula (II) | | | |
| --- | --- | --- | --- | --- |
| | | Substitute | | |
| Sr. No. | Structure | R5 | R6 | Characteristics |
| 1 | 4'-(2-Methyl-5-nitro-imidazol-1-ylmethyl)-biphenyl-2-carbonitrile | CH$_3$ | CN | M.P: 63° C. IR (KBr) (cm$^{-1}$): 3000, 2960, 2880, 2263, 1330. $^1$H NMR δ ppm in CDCl$_3$: 7.99 (1H), 7.12~7.62 (9H), 4.52 (2H), 2.42 (3H). |
| 2 | 4'-(4-Nitro-imidazol-1-ylmethyl)-biphenyl-2-carbonitrile | H | CN | M.P: 135-140° C. IR (KBr) (cm$^{-1}$): 3010, 2880, 2260 1338. NMR δ ppm in CDCl$_3$: 7.99 (1H), 7.12~7.66 (10H), 4.62 (2H). |

TABLE 2-continued

Compounds of Formula (II)

| Sr. No. | Structure | Substitute R5 | R6 | Characteristics |
|---|---|---|---|---|
| 3 | 4'-(5-Bromo-2-methyl-4-nitro-imidazol-1-ylmethyl)-biphenyl-2-carbonitrile | Br, CH$_3$ | CN | M.P: 158-162° C.<br>IR (KBr pellet) (cm$^{-1}$):<br>: 3050, 2250, 1550, 1340, 775.<br>$^1$H NMR δ ppm in CDCl$_3$:<br>7.970-7.277 (8H), 5.473 (2H), 2.428 (3H). |
| 4 | 4'-(5-Nitro-imidazol-1-ylmethyl)-biphenyl-2-carbonitrile | H | CN | M.P: 98-100° C.<br>IR (KBr pellet) (cm$^{-1}$):<br>3020, 2220, 1460.<br>$^1$H NMR δ ppm in CDCl$_3$: 7.99 (2H), 7.16-7.52 (8H), 4.18 (2H). |
| 5 | 4'-(4-Nitro-imidazol-1-ylmethyl)-biphenyl-2-carboxylic acid | H | COOH | M.P: 202-204° C.<br>IR (KBr) cm$^{-1}$: 3000, 2960, 2880, 2700, 1710, 1332.<br>$^1$H NMR δ ppm in CDCl$_3$: 11 (1H), 7.99 (1H), 7.12~7.66 (10H), 4.62 (2H). |
| 6 | 4'-(5-Nitro-imidazol-1-ylmethyl)-biphenyl-2-carboxylic acid | H | COOH | M.P: 144-146° C.<br>IR (KBr pellet) cm$^{-1}$: 3058, 3020, 1678, 1460.<br>$^1$H NMR (DMSO-d$_6$) (δ ppm):<br>10.01 (1H), 7.99 (2H), 7.12-7.52 (8H), 4.18 ( 2H). |
| 7 | 4'-(4-Nitro-2-methyl-imidazol-1-ylmethyl)-biphenyl-2-carboxylic acid | CH$_3$ | COOH | M.P: 240-244° C.<br>IR (KBr pellet) cm$^{-1}$: 3100, 3050, 1720, 1510, 1150, 850.<br>$^1$H NMR δ ppm in CDCl$_3$: 12.809 (1H), 8.499 (1H), 7.750-7.290 (8H), 5.332 (2H) and 2.325 (3H). |
| 8 | 4'-(5-Bromo-2-methyl-4-nitro-imidazol-1-ylmethyl)-biphenyl-2-carboxylic acid | Br, CH$_3$ | COOH | M.P: 222-225° C.<br>IR (KBr pellet) cm$^{-1}$: 3100, 3025, 1720, 1535, 1350, 831.<br>$^1$H NMR δ ppm in CDCl$_3$:<br>12.806 (1H), 7.738-7.197 (8H), 5.400 (2H), 2.396 (3H). |
| 9 | 4'-(4-Nitro-imidazol-1-ylmethyl)-biphenyl-2-carboxylic acid methyl ester | H | COOMe | M.P: 157-160° C.<br>IR (KBr pellet) cm$^{-1}$:<br>3125, 1790, 1490, 1175, 840.<br>$^1$H NMR δ ppm in CDCl$_3$:<br>7.914-7.252 (8H), 5.230 (1H), 3.687 (3H). |
| 10 | 5-[4'-(5-Nitro-imidazol-1-ylmethyl)-biphenyl-2-yl]-1H-tetrazole | H | 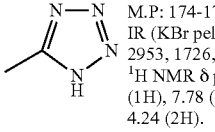 | M.P: 174-176° C.<br>IR (KBr pellet) cm$^{-1}$: 3317, 2953, 1726, 1405.<br>$^1$H NMR δ ppm in CDCl$_3$: 7.96 (1H), 7.78 (1H), 7.12~7.66 (9H), 4.24 (2H). |
| 11 | 5-[4'-(2-Methyl-5-nitro-imidazol-1-ylmethyl)-biphenyl-2-yl]-1H-tetrazole | CH$_3$ | 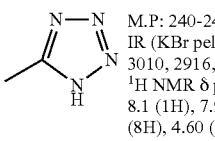 | M.P: 240-244° C.<br>IR (KBr pellet) cm$^{-1}$: 3313, 3010, 2916, 1695, 1410.<br>$^1$H NMR δ ppm in CDCl$_3$:<br>8.1 (1H), 7.99 (1H), 7.12-7.71 (8H), 4.60 (2H), 2.4 (3H). |
| 12 | 5-[4'-(4-Nitro-imidazol-1-ylmethyl)-biphenyl-2-yl]-1H-tetrazole | H | 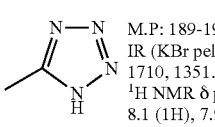 | M.P: 189-192° C.<br>IR (KBr pellet) cm$^{-1}$: 3310, 2960, 1710, 1351.<br>$^1$H NMR δ ppm in CDCl$_3$:<br>8.1 (1H), 7.99 (1H), 7.12~7.66 (9H), 5.01 (2H). |

Biological Evaluation:
Biological Activity Testing:
Animals

Male Wistar rats weighing 175-200 g and Swiss albino mice weighing 20-25 g were housed in the Animal Care Facility. The animals were fed standard laboratory feed and tap water. Unless otherwise noted, in all experiments described in the following text, the sample size in each group was at least 6.
Drugs Diclofenac Sodium, tolfenamic acid, and celecoxib were from the commercial market.
Statistical Analysis All data are expressed as mean _SEM. Groups of data were compared using a one-way analysis of variance followed by a Dennett's multiple comparison test. An associated probability (P value) of less than 5% was considered significant.
Analgesic Activity Against Acetic Acid Induced Writhing Pain was induced by injection of irritant i.e. acetic acid into the peritoneal cavity of mice. The animals react with a characteristic stretching behavior called writhing i.e. contractions of abdomen, turning of trunk and extension of hind limb, which was observed in various groups of animals. Vehicle (1% w/v carboxymethylcellulose (CMC), 0.5 ml per orally (p.o.)) was given to control group (n=6 per group) of mice. A mice in the test groups (n=6 per group) received test molecules at 10 mg/kg p.o.

Diclofenac sodium and tolfenamic acid (10 mg/kg) was used as the reference analgesic drug. One hour following the administration of test molecule, 0.1 ml/100 gm of 0.6% v/v acetic acid solution was injected intraperitoneally to each of the test mice. The number of writhes that occurred within the next 10 min following acetic acid administration was counted and recorded. Results were expressed as percentage inhibition of writhing.
In Vivo Screening Method, Carrageenan-Induced Rat Paw Edema Model Male Wistar rats (120-140 gm) were fasted for 16 hour before the experiment. Anti-inflammatory activity was evaluated by carrageenan-induced paw edema test in rats. Diclofenac sodium, tolfenamic acid and celecoxib at 10 mg/kg were administered as standard drugs for comparison. The test molecules were administered at dose level 10 mg/kg. Molecules were suspended in 0.25% carboxymethylcellulose (CMC) and administered orally in a volume of 10 ml/kg, 2 hour before carrageenan injection. Paw edema was induced in rats by intradermal injection of 50 µl, of 1% λ-carrageenan in saline into the planer surface of right hind paw. The volume of the injected paw was measured hourly thereafter for 4 hours using plethysmometer (Ugo-Basile, Italy). Paw edema was compared with vehicle controlled group and percentage inhibition was calculated.
Acute Oral Toxicity Studies Healthy adult albino mice of either sex weighing 20-25 gm, starved overnight were subjected to acute toxicity studies as per guidelines (AOT No. 425) suggested by Organization for Economic Co-operation and Development (OECD) 2001. The mice were observed continuously for 2 h for behavioral, neurological and autonomic profiles for any lethality or death for next 48 hrs. Based on the results obtained from this study, lethal dose ($LD_{50}$) was calculated.
Assessment of Gastric Ulcerogenic Effects in the Rat on Acute Administration of Drugs Groups of 6 male Wistar rats weighing 120-140 g were fasted for 24 h with free access to water. Test compounds and standard compounds (diclofenac sodium, tolfenamic acid and celecoxib) were given orally at 100 mg/kg to fasted animals, after 5 hours, the rats were killed for blind assessment of gastric damage. The lengths (in millimeters) of all hemorrhagic lesions were measured and the "gastric damage score" was calculated for each stomach by summing these values. After scoring the damage, a sample of the corpus region of each stomach was fixed in neutral buffered formalin for subsequent histologic assessment.

TABLE 1

Comparison of Analgesic and anti-inflammatory activity

| Structure | MW | Log p | Analgesic activity in Swiss albino mice (% inhibition) | Anti-inflammatory activity in Wistar rats (% inhibition) | |
|---|---|---|---|---|---|
| | | | | 3 h | 4 h |
| 4'-(2-Methyl-5-nitro-imidazol-1-ylmethyl)-biphenyl-2-carbonitrile | 318 | 1.492 | 84.25 | 19.52 | 24.25 |
| 4'-(4-Nitro-imidazol-1-ylmethyl)-biphenyl-2-carbonitrile | 304 | 2.04 | 86.61 | 35.82 | 44.28 |
| 4'-(4-Nitro-imidazol-1-ylmethyl)-biphenyl-2-carboxylic acid | 323 | 3.28 | 84.13 | 38.31 | 44.63 |
| Diclofenac sodium | 296 | 4.12 | 89.51 | 35.05 | 39.99 |
| Celecoxib | 327 | 4.34 | 77.0 | 45.24 | 45.32 |

TABLE 2

Results for toxicity study

| Code | $LD_{50\ mg/kg}$ | Gastric score* | Histopathology study (ulcerogenecity) Dose 100 mg/kg |
|---|---|---|---|
| Control group | — | 0.2 ± 0.2 | No sign of ulceration |
| Vehicle Group | — | 0.4 ± 0.4 | No sign of ulceration |
| 4'-(4-Nitro-imidazol-1-ylmethyl)-biphenyl-2-carbonitrile | 2000< | 1.83 ± 0.54 | No sign of ulceration |
| 4'-(4-Nitro-imidazol-1-ylmethyl)-biphenyl-2-carboxylic acid | 2000< | 1.6 ± 0.50 | No sign of ulceration |
| Tolfenamic acid | 550> less than | 9 ± 2.1 | Shows sign of ulceration Mucosal changes observed |
| Diclofenac sodium | 175> less than | 11 ± 3.6 | Shows sign of ulceration Mucosal changes observed |
| Celecoxib | 2000> less than | 1.8 ± 0.62 | No sign of ulceration |

*Results are expressed as the mean_SEM for 6 rats per group.

Examples of Compositions and Process of their Preparation
1) Example. Capsule

| Name of compound | quantity |
|---|---|
| 4'-(4-Nitro-imidazol-1-ylmethyl)-biphenyl-2-carboxylic acid | 10 mg |

0.01.gms of 4'-(4-Nitro-imidazol-1-ylmethyl)-biphenyl-2-carboxylic acid powder having bulk density of more than 0.5 was taken, sifted. It was filled in capsule of size 0. The capsule is ready for administration. If the quantity of compound filled in capsule is in the range of 50 mg to 100 mg, capsules of smaller size can be used. In one embodiment, the powder of the compound is mixed with diluents and subsequently filled in capsules. This requires capsules of bigger size. By varying the quantity of diluent Lactose, capsules of different sizes can be used. This is illustrated by following example:

| (1) Compound of the invention | 10 mg |
| (2) Lactose | 400 mg |
| (3) Corn starch | 12 mg |
| (4) Magnesium sterate | 1 mg |

2) Example of Tablet Composition

| (1) Compound of the invention | 50 mg |
| (2) Lactose | 200 mg |

Tablets of the compound are prepared using direct compression technique known to the persons skilled in the art where by the compound is mixed with directly compressible excipient so as to give 50 mg of compound per tablet. The tablet weight can be adjusted as per individual needs.

Alternative process to prepare tablet composition involves dry mixing of suitable excipients followed by wet granulation by conventional methods known to the persons skilled in the art, optional drying sizing, lubrication and compression. Compressed tablets are optionally coated with known techniques of film coating, sugar coating. These steps are carried out so as to give tablets having 0.02 to 2000 mg of active compound.

We claim:

1. Biphenyl imidazole compounds of Formula (I) and compound of Formula (II) or their salts,

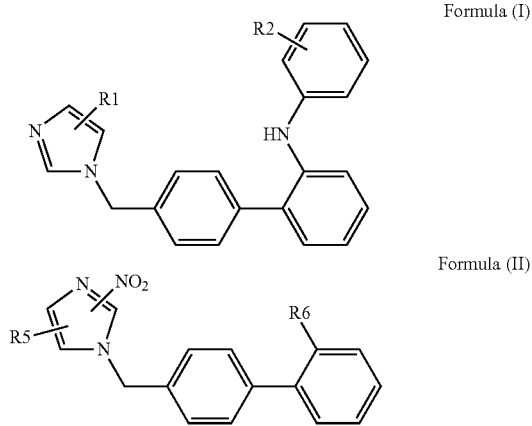

Formula (I)

Formula (II)

wherein
compound of the Formula (I) is substituted with one or more of R1 groups in imidazole ring;
wherein,
R1 is H, —$NO_2$, R4, —O—R4, —$NH_2$, —$SO_2NH_2$, —$NHSO_2$—R4, halo, —COOH, —CHO, —CN;
R2 is H, —O—$(CH_2)_n$-R4 wherein n=0 to 5, —$NO_2$, —$SO_2NH_2$, —$NHSO_2$—R4, —CN, —COOH, halo, optionally substituted amino group, R4, cyclo alkyl group, alkyl thio, acyl group, substituted or unsubstituted heterocyclic group, alkoxy carbonyl, aryloxy, aryloxy carbonyl, substituted or unsubstituted amide;
R4 is any substituted or unsubstituted alkyl of C1 to C20 carbon chain; and compound of Formula (II) is substituted with one or more of R5 in nitro imidazole ring,
wherein,
R5 is one or more of H, halo, $NO_2$, R4, alkoxy carbonyl, —O—$(CH_2)_n$-R4 wherein n is 0 to 5, —COOH, —$SO_2NH_2$, —NHSO2-R4, aryl, cycloalkyl, benzyl or substituted benzyl optionally substituted on phenyl ring with at least one halogen, CN, —$(CH_2)_m$-R7 wherein m is 0 to 5, —$(CH_2)_p$-OC(O)R4 wherein p is 1 to 5, substituted or unsubstituted amine;
R6 is one or more of CN, H, halo, $NO_2$, —$NH_2$, R4, alkoxy carbonyl, —O—$(CH_2)_n$-R4 wherein n is 0 to 5, —COOH, —$SO_2NH_2$, —$NHSO_2$—R4, $SO_2$—NH—R4, aryl, substituted or unsubstituted heterocyclic group, —$CH_2$COOH, —$CH_2$COOR4, —$SO_3$H, —$PO_3$H, substituted or unsubstituted amide, —$CH_2$-R7, —CONH—R7 wherein R7 is any substituted or unsubstituted heterocyclic group and
R4 is any substituted or unsubstituted alkyl of C1 to C20 carbon chain.

2. A process for the preparation of biphenyl imidazole compounds of Formula (I) or its salts, thereof wherein
4'-substituted imidazole biphenyl-2-amine is treated with equimolar quantities of optionally substituted phenyl halo compound and potassium carbonate in presence of catalytic amount of copper, cuprous bromide or cuprous acetate and aprotic solvent such as dimethylformamide, dimethylacetamide, dimethylsulfoxide at a temperature of 0° C. to 150° C., preferably at 130° C. to 150° C. for 4 to 16 hours, preferably for 6 to 10 hours to give Formula (I).

3. A process for the preparation of biphenyl imidazole compounds of Formula (II) or its salts, thereof wherein
4'-substituted nitroimidazole biphenyl-2-carbonitrile is treated with potassium hydroxide in alcohols preferably such as methanol, ethanol, isopropanol, butanol at a temperature of 0° C. to 70° C., preferably at 50° C. to 70° C. for 4 to 16 hours, preferably for 8 to 12 hours to give Formula (II) (wherein R6 is COOH).

4. A process for the preparation of biphenyl imidazole compounds of Formula (II) or its salts, thereof wherein
4'-substituted nitroimidazole biphenyl-2-carbonitrile is treated with sodium azide and catalytic amount of ammonium chloride is added in aprotic solvent such as dimethylformamide, dimethylacetamide, dimethylsulfoxide at a temperature of 0° C. to 150° C., preferably at 130° C. to 150° C. for 8 to 20 hours, preferably for 12 to 16 hours to give Formula (II) (wherein R6 is tetrazol).

5. Biphenyl imidazole compounds
(4-methoxy phenyl)-[4'-(2-methyl imidazol-1-ylmethyl)-biphenyl-2-yl]-amine;
[4'-(2-methyl-imidazol-1-ylmethyl)-biphenyl-2-yl]-phenyl-amine;
[4'-(2-methyl-4-nitro-imidazol-1-ylmethyl)-biphenyl-2-yl]-phenyl-amine;
4-[4'-(2methyl-4-nitro-imidazol-1-ylmethyl)-biphenyl-2-ylamino]-benzenesulfonamide;
[4'-(2-bromomethyl imidazol-1-ylmethyl)-biphenyl-2-yl]-(4-methoxyphenyl)-amine;
[4'-(2-bromomethyl-4-nitro-imidazol-1-ylmethyl)-biphenyl-2-yl](4-sulfonamidophenyl)-amine;
4-[4'-(2-hydroxymethyl-4-nitro-imidazol-1-ylmethyl)-biphenyl-2-ylamino]- benzenesulfonamide;
{1-[2'-(4-methoxy-phenylamino)-biphenyl-4-ylmethyl]-1H-imidazol-2-yl}-methanol;
(4'-imidazol-1-ylmethyl-biphenyl-2-yl)-(4-nitro-phenyl)-amine;

N-[4-(4'imidazol1ylmethyl biphenyl-2-ylamino)-phenyl]-methanesulfonamide;
4'-(2-methyl-5-nitro imidazol-1-ylmethyl)-biphenyl-2-carbonitrile;
4'-(2-methyl-5-nitro-imidazol-1-ylmethyl)-biphenyl-2-sulfonic acid amide;
4'-(5-bromo-2-methyl-4-nitro-imidazol-1-ylmethyl)-biphenyl-2-carbonitrile;
N-[4'-(5-nitro-imidazol-1-ylmethyl)-biphenyl-2-yl]-methanesulfonamide;
4'-(5-nitro-imidazol-1-ylmethyl)-biphenyl-2-carboxylic acid;
5-[4'-(5-nitro-imidazol-1-ylmethyl)-biphenyl-2-yl]-1H-tetrazole;
4'-(2-methyl-5-nitro-imidazol-1-ylmethyl)-biphenyl-2-sulfonic acid methylamide;
4'-(4-nitro-2-methyl-imidazol-1-ylmethyl)-biphenyl-2-carboxylic acid;
4'-(5-bromo-2-methyl-4-nitro-imidazol-1-ylmethyl)-biphenyl-2-carboxylic acid;
4'-(4-nitro-imidazol-1-ylmethyl)-biphenyl-2-carboxylic acid methyl ester;
5-[4'-2-methyl-5-nitro-imidazol-1-ylmethyl)-biphenyl-2-yl]-1H-tetrazole;
4'-(4-nitro-imidazol-1-ylmethyl)-biphenyl-2-carbonitrile;
4'-(5-nitro-imidazol-1-ylmethyl)-biphenyl-2-carbonitrile;
4'-(4-nitro-imidazol-1-ylmethyl)-biphenyl-2-carboxylic acid;
5-[4'-(4-nitro-imidazol-1-ylmethyl)-biphenyl-2-yl]-1H-tetrazole.

6. A pharmaceutical composition comprising at least one biphenyl imidazole compound of Formula (I) or compound of Formula (II) as claimed in claim 1 or in claim 5, or its salts, in association with at least one pharmacologically acceptable excipient.

7. A pharmaceutical composition as claimed in claim 6, wherein biphenyl imidazole compound is
(4-methoxy phenyl)-[4'-(2-methyl imidazol-1-ylmethyl)-biphenyl-2-yl]-amine;
[4'-(2-methyl-imidazol-1-ylmethyl)-biphenyl-2-yl]-phenyl-amine;
[4'-(2-methyl-4-nitro-imidazol-1-ylmethyl)-biphenyl-2-yl]-phenyl-amine;
4-[4'-(2methyl-4-nitro-imidazol-1-ylmethyl)-biphenyl-2-ylamino]-benzenesulfonamide;
[4'-(2-bromomethyl imidazol-1-ylmethyl)-biphenyl-2-yl]-(4-methoxyphenyl)-amine;
[4'-(2-bromomethyl-4-nitro-imidazol-1-ylmethyl)-biphenyl-2-yl](4-sulfonamidophenyl)-amine;
4-[4'-(2-hydroxymethyl-4-nitro-imidazol-1-ylmethyl)-biphenyl-2-ylamino]- benzenesulfonamide;
{1-[2'-(4-methoxy-phenylamino)-biphenyl-4-ylmethyl]-1H-imidazol-2-yl}-methanol;
(4'-imidazol-1-ylmethyl-biphenyl-2-yl)-(4-nitro-phenyl)-amine;
N-[4-(4'imidazol1ylmethyl biphenyl-2-ylamino)-phenyl]-methanesulfonamide;
4'-(2-methyl-5-nitro imidazol-1-ylmethyl)-biphenyl-2-carbonitrile;
4'-(2-methyl-5-nitro-imidazol-1-ylmethyl)-biphenyl-2-sulfonic acid amide;
4'-(5-bromo-2-methyl-4-nitro-imidazol-1-ylmethyl)-biphenyl-2-carbonitrile;
N-[4'-(5-nitro-imidazol-1-ylmethyl)-biphenyl-2-yl]-methane sulfonamide;
4'-(5-nitro-imidazol-1-ylmethyl)-biphenyl-2-carboxylic acid;
5-[4'-(5-nitro-imidazol-1-ylmethyl)-biphenyl-2-yl]-1H-tetrazole;
4'-(2-methyl-5-nitro-imidazol-1-ylmethyl)-biphenyl-2-sulfonic acid methylamide;
4'-(4-nitro-2-methyl-imidazol-1-ylmethyl)-biphenyl-2-carboxylic acid;
4'-(5-bromo-2-methyl-4-nitro-imidazol-1-ylmethyl)-biphenyl-2-carboxylic acid;
4'-(4-nitro-imidazol-1-ylmethyl)-biphenyl-2-carboxylic acid methyl ester;
5-[4'-2-methyl-5-nitro-imidazol-1-ylmethyl)-biphenyl-2-yl]-1H-tetrazole;
4'-(4-nitro-imidazol-1-ylmethyl)-biphenyl-2-carbonitrile;
4'-(5-nitro-imidazol-1-ylmethyl)-biphenyl-2-carbonitrile;
4'-(4-nitro-imidazol-1-ylmethyl)-biphenyl-2-carboxylic acid;
5-[4'-(4-nitro-imidazol-1-ylmethyl)-biphenyl-2-yl]-1H-tetrazole.

8. The composition as claimed in claim 6, wherein the composition is solid dosage form or liquid dosage form or semi-solid dosage form.

9. The composition as claimed in claim 6, for internal use or external application.

10. The process for the preparation of composition comprising biphenyl irnidazole compounds of Formula (I) and compound of Formula. (II) or their salts, comprising bringing the biphenyl imidazole compounds of Formula (I) and compound of Formula (II) optionally in contact with at least one pharmacologically acceptable excipient, optionally mixing or granulating, drying, compressing coating it to formulate into solid dosage form; or
dissolving it or suspending it or solvating it and optionally filtering it or homogenizing it or milling it to formulate it into a liquid dosage form; or incorporating it into an aqueous or nonaqueous or suitable base and optionally homogenizing the mass or milling the mass to formulate it into a semi-solid dosage form composition.

11. A method of treatment of inflammation in living bodies comprising administering to a patient biphenyl imidazole compounds of Formula (I) and compound of Formula (II) or their salts, or the compositions comprising biphenyl imidazole compounds of Formula (I) and compound of Formula (II).

12. A pharmaceutical composition comprising at least one biphenyl imidazole compound of Formula (I) or compound of Formula (II) as claimed in claim 5, wherein the compound of Formula (I) or compound of Formula (II) is present in the range of 0.001 mg to 5 gms.

\* \* \* \* \*